(12) United States Patent
Takahashi et al.

(10) Patent No.: US 8,877,884 B2
(45) Date of Patent: Nov. 4, 2014

(54) ADHESIVE COMPOSITION, FILM ADHESIVE, AND METHOD FOR PRODUCING THE ADHESIVE COMPOSITION

(75) Inventors: Motoki Takahashi, Kawasaki (JP); Hirofumi Imai, Kawasaki (JP); Takahiro Asai, Kawasaki (JP); Koichi Misumi, Kawasaki (JP); Toshiyuki Ogata, Kawasaki (JP)

(73) Assignee: Tokyo Ohka Kogyo Co., Ltd., Kanagawa (JP)

( * ) Notice: Subject to any disclaimer, the term of this patent is extended or adjusted under 35 U.S.C. 154(b) by 756 days.

(21) Appl. No.: 12/458,259

(22) Filed: Jul. 7, 2009

(65) Prior Publication Data

US 2010/0010182 A1    Jan. 14, 2010

(30) Foreign Application Priority Data

Jul. 8, 2008  (JP) ................. 2008-178095

(51) Int. Cl.
| | | |
|---|---|---|
| *C08F 212/08* | (2006.01) | |
| *C09J 7/02* | (2006.01) | |
| *C09J 125/04* | (2006.01) | |
| *C09J 133/04* | (2006.01) | |
| *C09J 135/00* | (2006.01) | |
| *C08F 6/10* | (2006.01) | |
| *C08F 6/12* | (2006.01) | |
| *C09J 125/14* | (2006.01) | |
| *C08F 220/12* | (2006.01) | |
| *C08J 3/09* | (2006.01) | |
| *C09J 133/24* | (2006.01) | |
| *C09J 125/08* | (2006.01) | |
| *C09J 135/06* | (2006.01) | |
| *C07B 63/00* | (2006.01) | |
| *C08F 6/00* | (2006.01) | |
| *C08F 220/14* | (2006.01) | |
| *C08F 220/18* | (2006.01) | |
| *C08F 222/40* | (2006.01) | |

(52) U.S. Cl.
CPC *C09J 7/02* (2013.01); *C09J 125/04* (2013.01); *C09J 133/04* (2013.01); *C09J 135/00* (2013.01); *C08J 2325/08* (2013.01); *C08F 6/10* (2013.01); *C08F 6/12* (2013.01); *C08F 212/08* (2013.01); *C08J 2325/14* (2013.01); *C09J 125/14* (2013.01); *C08F 220/12* (2013.01); *C08J 3/095* (2013.01); *C09J 133/24* (2013.01); *C09J 125/08* (2013.01); *C09J 135/06* (2013.01); *C07B 63/00* (2013.01); *C08F 6/001* (2013.01); *C08F 220/14* (2013.01); *C08F 2220/1825* (2013.01); *C08F 2222/402* (2013.01)
USPC .......................... 526/346; 526/262

(58) Field of Classification Search
CPC ........... C07B 63/00; C08F 6/001; C08F 6/10; C08F 6/12; C08F 220/12; C08F 220/14; C08F 212/08; C08F 2220/1825; C08F 2220/52; C08J 3/095; C08J 2325/08; C08J 2325/14; C08J 125/04; C08J 135/06; C08J 133/24
USPC .................................................. 526/262, 346
See application file for complete search history.

(56) References Cited

U.S. PATENT DOCUMENTS

| | | | | |
|---|---|---|---|---|
| 3,591,658 | A * | 7/1971 | Onishi et al. ................... | 525/269 |
| 4,248,982 | A * | 2/1981 | Bi et al. ........................ | 525/271 |
| 4,988,770 | A * | 1/1991 | Wong ............................. | 525/244 |
| 5,079,090 | A * | 1/1992 | Joseph et al. .................. | 428/343 |
| 5,708,112 | A * | 1/1998 | Kihara et al. .................. | 526/340 |
| 6,602,599 | B1 | 8/2003 | Toyoda et al. | |
| 7,268,061 | B2 | 9/2007 | Miyanari et al. | |
| 2005/0170612 | A1 | 8/2005 | Miyanari et al. | |
| 2006/0155062 | A1* | 7/2006 | De Keyzer ..................... | 525/88 |
| 2009/0137760 | A1 | 5/2009 | Misumi et al. | |

FOREIGN PATENT DOCUMENTS

| | | |
|---|---|---|
| JP | 61-158145 | 7/1986 |
| JP | 04-314773 | 11/1992 |
| JP | 2001-55546 | 2/2001 |
| JP | 2001-279208 | 10/2001 |
| JP | 2003-173993 | 6/2003 |
| JP | 2007-119646 | 5/2007 |

OTHER PUBLICATIONS

Computer generated English translation of the Japanese Office Action issued on Jan. 7, 2014 in corresponding JP Application No. 2008-178095.*
Office Action issued Feb. 12, 2013 in corresponding Japanese Application No. 2008-178095.

* cited by examiner

*Primary Examiner* — Richard A Huhn
(74) *Attorney, Agent, or Firm* — Wenderoth, Lind & Ponack, L.L.P.

(57) ABSTRACT

An adhesive composition is disclosed which includes a polymer prepared by copolymerizing a monomer containing a polymerizable group, the polymer including a low-molecular-weight component having a molecular weight equivalent to 1% or less of the weight-average molecular weight of the polymer, the low-molecular-weight component is contained in a range of not less than 0 weight % to less than 0.3 weight % of the total weight of the polymer. This allows provision of an adhesive composition having great adhesive strength in a high-temperature environment, especially at temperatures from 140° C. to 200° C., as well as high heat resistance and favorable crack resistance.

1 Claim, No Drawings

ADHESIVE COMPOSITION, FILM ADHESIVE, AND METHOD FOR PRODUCING THE ADHESIVE COMPOSITION

This Nonprovisional application claims priority under 35 U.S.C. §119(a) on Patent Application No. 2008-178095 filed in Japan on Jul. 8, 2008, the entire contents of which are hereby incorporated by reference.

TECHNICAL FIELD

The present invention relates to an adhesive composition, a film adhesive, and a method of producing the adhesive composition. More specifically, the present invention relates to an adhesive composition, a film adhesive, and a method of producing the adhesive composition, each for temporarily fixing a sheet or a protection board to a semiconductor product, in a step of carrying out processing such as grinding of semiconductor products (e.g., semiconductor wafer), optical products, and the like.

Background Art

In recent years, due to multiple functioning of mobile phones, digital AV devices, IC cards, and the like, demands have been increasing for downsizing, reduction in thickness, and high integration of semiconductor silicon chips (hereinafter referred to as "chips"). For example, the reduction of thickness is demanded for integrated circuits in which a plurality of chips are integrated, as typified by CSP (chip size package) and MCP (multi-chip package). Among these integrated circuits, a system-in-package (SiP) in which a plurality of semiconductor chips are mounted in a single semiconductor package has become an extremely important technique in order to accomplish downsizing, reduction in thickness, and high integration of chips that are installed in the semiconductor package. The downsizing, reduction in thickness and high integration enables realization of multiple functioning, downsizing, and reduction of weight of electronic devices.

In order to respond to the needs for a thin product, it is required to reduce the thickness of a chip to not more than 150 µm. Further, it is required to process the chip so that its thickness is reduced to not more than 100 µm for the CSP and the MCP, and not more than 50 µm for the IC card.

Conventionally, SiP products are manufactured by use of a method in which respective bumps (electrodes) provided on each of stacked chips are wired to a circuit board by a wire bonding technique. In order to respond to the demand for the reduction in thickness and high integration, a through-hole electrode technique is required, not the wire bonding technique. The through-hole electrode technique is a technique in which (i) chips each having a through-hole electrode are stacked and (ii) a bump is formed on a backside of the chips thus stacked.

A thin chip is manufactured by, for example, in a method as follows: (i) a high purity single crystal silicon or the like is sliced to a wafer form, (ii) a predetermined circuit pattern of an IC or the like is formed on a surface of the wafer by etching the surface of the wafer so that an integrated circuit is built, (iii) a back surface of the semiconductor wafer thus obtained is grinded by use of a grinder, and (iv) after the semiconductor wafer is grinded to a predetermined thickness, the semiconductor wafer is diced so as to form a chip shape. At this time, the predetermined thickness is around a range of 100 µm to 600 µm. Further, in a case where a through-hole electrode is to be formed, the wafer is grinded to a thickness of around a range of 50 µm to 100 µm.

In the manufacture of the semiconductor chip, the semiconductor wafer readily breaks in a case where external force is given to the wafer in the grinding step or at the time when the wafer is carried to the dicing step. This is because the semiconductor wafer is thin and fragile, and because circuit patterns are unlevel. Moreover, in the grinding step, purified water is used to clean the back surface of the semiconductor wafer for removing grinding dust and heat generated at the time of grinding, while grinding process is carried out. At this time, there is the need to prevent contamination of a circuit pattern surface due to the purified water used in cleaning.

Accordingly, in order to protect the circuit pattern surface of the semiconductor wafer and prevent breakage of the semiconductor wafer, a film adhesive for processing is attached on the circuit pattern surface while the grinding process is carried out.

Moreover, at the time of the dicing, the semiconductor wafer is diced in a state in which a protection sheet is attached to a back surface of the semiconductor wafer so that the semiconductor wafer is fixed. Chips obtained by the dicing are pushed up by use of a needle from a film base material side, and are fixed on a die pad.

Known types of film adhesives for processing and protection sheets as such include, for example, ones in which an adhesive layer made of an adhesive composition is provided on a base material film such as polyethylene terephthalate (PET), polyethylene (PE), polypropylene (PP), or ethylene-vinyl acetate copolymer (EVA) (for example, Patent Document 1 (Japanese Patent Application Publication, Tokukai, No. 2003-173993 A (Publication Date: Jun. 20, 2003), Patent Document 2 (Japanese Patent Application Publication, Tokukai, No. 2001-279208 A (Publication Date: Oct. 10, 2001)).

Moreover, due to multilayer interconnection of semiconductor elements, a process is conducted such that: (i) a protection board is adhered, by use of the adhesive composition, to a surface of the semiconductor wafer on which a circuit is formed; (ii) a back surface of the semiconductor wafer is polished; (iii) the back surface thus polished is etched to form a mirror plane; and (iv) a back surface circuit is formed on the mirror plane. In this case, the protection board is adhered to the semiconductor wafer until the back surface circuit is formed (Patent Document 3 (Japanese Patent Application Publication, Tokukaisho, No. 61-158145 (Publication Date: Jul. 17, 1986)).

However, the following problem occurs in a case where the conventional film adhesive for processing and the like are used in steps which require high-temperature processing and high vacuum processing, as like in formation of the through-hole electrode: a problem of poor adhesion caused by insufficient adhesive strength in a high-temperature environment or generation of gas in a high vacuum environment.

For example, in the formation of the through-hole electrode, when semiconductor chips are connected to each other after formation of a bump on each of the semiconductor chips, a process is required which applies heat to the semiconductor chips to approximately 200° C., and further has the semiconductor chips to be in a high vacuum state. However, the adhesive composition which constructs an adhesive layer of a protection tape according to Patent Documents 1 and 2 has no resistance against such a high temperature of 200° C. Moreover, gas is generated due to application of heat. This gas causes the poor adhesion.

The processing method of the semiconductor substrate according to Patent Document 3 carries out a mirror surfacing process by use of an etching liquid and formation of a metal film by vacuum plating. In order to carry out these processes, the adhesive composition for adhering a protection board to a semiconductor wafer requires heat resistance and stripping property. However, Patent Document 3 includes no disclosure regarding formation of the adhesive composition.

The inventors found that the following problems occur even when the adhesive which uses such acrylic resin material is used:

Adhesive strength is weak in a high-temperature environment, due to an occurrence of a bubble-form strip on an adhesive surface at the time when the adhesive layer and the protection board are thermally compressed together, caused by generation of gas from moisture absorbed by the adhesive layer. Such generation of gas causes problems, not only that the adhesive strength is weakened in the high-temperature environment, but also difficulty in production and maintenance of a vacuum environment in a case where processing is carried out under vacuum conditions.

The adhesive composition for adhering a protection board to a semiconductor wafer further requires prevention of cracks.

The present invention has been accomplished in view of the above issues. It is an object of the present invention to provide an adhesive composition having great adhesive strength in a high-temperature environment, especially at temperatures from 140° C. to 200° C., as well as high heat resistance and favorable crack resistance.

Summary of Invention

A first mode of the present invention is an adhesive composition including a polymer prepared by polymerizing a monomer composition containing a polymerizable group, wherein: the polymer includes a low-molecular-weight component having a molecular weight equivalent to 1% or less of a weight-average molecular weight of the polymer; and the low-molecular-weight component is contained in a range of not less than 0 weight % to less than 0.3 weight % of a total weight of the polymer.

A second aspect of the present invention is a film adhesive including: a film; and an adhesive layer on the film, containing the adhesive composition of the present invention.

A third aspect of the present invention is a method of producing an adhesive composition including a polymer prepared by copolymerizing a monomer composition containing a polymerizable group, the method including the step of: removing, from a reaction solution containing the polymer, a low-molecular-weight component included in the polymer and having a molecular weight equivalent to 1% or less of a weight-average molecular weight of the polymer; wherein, during the step, a poor solvent is added to the reaction solution so that the polymer precipitated is recovered.

Additional objects, features, and strengths of the present invention will be made clear by the description below.

DESCRIPTION OF EMBODIMENTS

One embodiment of the present invention is described below with reference to the attached drawings. The present invention is not limited to the descriptions below, but may be modified as appropriate within the gist of the present invention besides the foregoing embodiments and examples.

[1. Adhesive Composition]

The present invention provides an adhesive composition including a polymer prepared by polymerizing a monomer containing a polymerizable group, wherein: the polymer includes a low-molecular-weight component having a molecular weight equivalent to 1% or less of a weight-average molecular weight of the polymer; and the low-molecular-weight component is contained in a range of not less than 0 weight % to less than 0.3 weight % of a total weight of the polymer. Note that the word "weight" as used in the present specification is used interchangeably with the word "mass."

The polymerizable group encompasses, for example, polymerizable functional groups, radical polymerizable groups, and photopolymerizable groups. More specifically, the polymerizable group encompasses, for example, an acrylic group, methacrylic group, allyl group, acryloyl group, and maleimide group.

[Monomer]

The monomer polymerized to prepare the polymer included in the adhesive composition of the present invention may be any monomer containing a polymerizable group. Examples of such a monomer encompass: styrene and derivatives thereof; a (meth)acrylic acid ester; and an N-alkylmaleimide. The following describes preferable examples of each monomer. The monomer of the present invention may be used solely. Alternatively, it may be replaced by a copolymer prepared with multiple kinds of monomers.

[Styrene]

The monomer for preparation of the polymer included in the adhesive composition of the present invention may be styrene or a derivative thereof. Properties of the styrene do not change even in a high-temperature environment of not less than 200° C. This allows improvement in heat resistance of the adhesive composition.

The derivative of styrene is not particularly limited to a specific one. It is, for example, α-methylstyrene, styrene, and 4-methylstyrene.

When at least one of styrene and a derivative thereof is used in combination with another monomer, the amount of such styrene and/or the derivative is not particularly limited, provided that the amount allows the occurrence of copolymerization reaction with the other monomer. The amount may be set as appropriate, for example, in accordance with target properties of the adhesive composition, such as adhesive strength and heat resistance. The amount is preferably not less than 30 parts by mass and not more than 70 parts by mass, and is more preferably not less than 30 parts by mass and not more than 55 parts by mass where the total amount of the monomers is 100 parts by mass. The amount of not less than 30 parts by mass improves the heat resistance, whereas the amount of not more than 70 parts by mass prevents decrease in the crack resistance.

[(Meth)acrylic Acid Ester]

Examples of the (meth)acrylic acid ester encompass: an alkyl (meth)acrylate having a chain structure; a (meth)acrylic acid ester having an aliphatic ring; and a (meth)acrylic acid ester having an aromatic ring.

Examples of the alkyl (meth)acrylate having a chain structure encompass acrylic long chain alkyl ester having a C15 to C20 alkyl group, and acrylic alkyl ester having a C1 to C14 alkyl group.

Examples of the acrylic long chain alkyl ester encompass: an alkyl ester of an acrylic or methacrylic acid, whose alkyl group is an n-pentadecyl group, an n-hexadecyl group, an n-heptadecyl group, an n-oxtadecyl group, an n-nonadecyl group, n-eicosyl group, or the like. Note that the alkyl group may be of a branched state.

Publicly known acrylic alkyl esters that are used in existing acrylic adhesives are examples of the acrylic alkyl esters having the C1 to C14 alkyl group. Examples of these acrylic alkyl esters are, for example, alkyl esters of acrylic or methacrylic acid whose alkyl group is a methyl group, an ethyl group, a propyl group, a butyl group, a 2-ethylhexyl group, an isooctyl group, an isononyl group, an isodecyl group, a dodecyl group, a lauryl group, a tridecyl group, or the like.

Examples of the (meth)acrylic acid ester having an aliphatic ring encompass: cyclohexyl(meth)acrylate, cyclopentyl(meth)acrylate, 1-adamantyl(meth)acrylate, norbornyl (meth)acrylate, isobornyl(meth)acrylate, tricyclodecanyl (meth)acrylate, and tetracyclododecanyl(meth)acrylate. Among the above, isobornyl methacrylate is preferable.

The (meth)acrylic acid ester having an aromatic ring is not particularly limited to a specific one; e.g., a phenyl group, a benzyl group, a tolyl group, a xylyl group, a biphenyl group, a naphthyl group, an anthracenyl group, a phenoxymethyl group, and a phenoxyethyl group. The aromatic ring may include a chained or branched C1 to C5 alkyl group; specifically, it is preferably phenoxyethyl acrylate. The use of the (meth)acrylic acid ester having an aromatic ring allows further improvement in the flexibility of the adhesive composition to be obtained. Specifically, a small amount of the (meth) acrylic acid ester having an aromatic ring provides flexibility as desired. This allows increase in the amount of the component that raises the glass transition temperature of the adhesive composition and also provision of an adhesive composition having high flexibility and great adhesive strength in a high-temperature environment.

When the (meth)acrylic acid ester is used in combination with another monomer, the amount of the (meth)acrylic acid ester is not particularly limited, provided that the amount allows the occurrence of copolymerization reaction with the other monomer. The amount may be set as appropriate, for example, in accordance with target properties of the adhesive composition, such as adhesive strength and heat resistance. The amount is preferably not less than 30 parts by mass and not more than 70 parts by mass, and is more preferably not less than 40 parts by mass and not more than 60 parts by mass where the total amount of the monomers is 100 parts by mass. The amount of not less than 30 parts by mass improves the heat resistance, whereas the amount of not more than 70 parts by mass prevents decrease in the crack resistance.

[N-alkylmaleimide]

The N-alkylmaleimide is not particularly limited to a specific one. Examples of the N-alkylmaleimide encompass N-methylmaleimide, N-ethylmaleimide, N-n-propylmaleimide, N-isopropylmaleimide, N-n-butylmaleimide, N-isobutylmaleimide, N-sec-butylmaleimide, N-tert-butylmaleimide, N-n-pentylmaleimide, N-n-hexylmaleimide, N-n-heptylmaleimide, N-n-octylmaleimide, N-laurylmaleimide, N-stearylmaleimide, N-cyclohexylmaleimide. Among the above, N-cyclohexylmaleimide is preferable.

When the N-alkylmaleimide is used in combination with another monomer, the amount of the N-alkylmaleimide is not particularly limited, provided that the amount allows the occurrence of copolymerization reaction with the other monomer. The amount may be set as appropriate, for example, in accordance with target properties of the adhesive composition, such as adhesive strength and heat resistance. The amount of the N-alkylmaleimide to be contained is preferably not less than 1 part by mass and not more than 50 parts by mass, and is more preferably not less than 5 parts by mass and not more than 30 parts by mass where the total amount of the monomers is 100 parts by mass. The amount of not less than 1 part further improves the heat resistance of the adhesive layer to be obtained, as well as its adhesive strength in a high-temperature environment, whereas the amount of not more than 50 parts by mass further facilitates stripping off after high-temperature processing.

[Low-Molecular-Weight Component]

The word "low-molecular-weight component" as used in the present specification refers to a compound having a molecular weight equivalent to 1% or less of the weight-average molecular weight of the polymer included in the adhesive composition of the present invention.

The weight-average molecular weight of the polymer is not particularly limited. It is preferably not less than 10,000 and not more than 300,000, is more preferably not less than 20,000 and not more than 200,000, and is even more preferably not less than 30,000 and not more than 150,000. The weight-average molecular weight of not less than 10,000 provides better flexibility, whereas that of not more than 300,000 provides better heat resistance.

The weight-average molecular weight may be measured by GPC. The term "weight-average molecular weight" as used in the present specification refers to a value obtained by measurement made under the following conditions:

Standard Polymer: polystyrene
Apparatus: HLS-8220 GPC available from TOSOH Corporation
Detector: refractive index (RI) detector
Column: TSK Gel Super (a set of three) available from TOSOH Corporation
Column Temperature: 40° C.
Sample: a measurement sample prepared by dissolution of 0.02 g of copolymer powder in 10 ml of tetrahydrofuran (THF)
Amount Injected: 40 μl
Flow Rate: 0.6 ml/min
Developing Solvent: THF The low-molecular-weight component is not limited to a specific one, provided that it is a compound having a molecular weight equivalent to 1% or less of the weight-average molecular weight of the polymer. Examples of the low-molecular-weight component encompass: unpolymerized residual monomers; oligomers; polymerization initiators and the like; and substances obtained as a result of bonding of polymerization initiators with each other.

The low-molecular-weight component contained in an amount of less than 0.3 weight % or not contained (i.e., contained in an amount of 0 weight %) provides favorable heat resistance and crack resistance and also reduces degassing. Improvement in the heat resistance of a polymer is generally achievable by, for example, increase in the molecular weight of the polymer. In contrast, this is achieved in the present invention by reduction in the content of the low-molecular-weight component, which then increases the weight-average molecular weight of the polymer included in the adhesive composition.

The content of the low-molecular-weight component is not limited, provided that it is, as described above, not less than 0 weight % and less than 0.3 weight %. The content is preferably not less than 0 weight % and not more than 0.1 weight %, and is more preferably not less than 0 weight % and not more than 0.01 weight %. The content of not less than 0 weight % and not more than 0.1 weight % provides better heat resistance and crack resistance and also further reduces degassing.

[Components in the Adhesive Composition other than the Polymer]

The adhesive composition according to the present invention may further include, to an extent in which essential properties of the present invention is not lost, miscible additives, for example, a commonly used addition resin, plasticizing agent, adhesive auxiliary agent, stabilization agent, coloring agent, and surface active agent, each of which improves effectiveness of the adhesive.

Further, the polymer of the adhesive composition may be dissolved in an organic solvent. Examples of the organic solvent encompass: ketones such as acetone, methyl ethyl ketone, cyclohexanone, methyl isoamyl ketone, and 2-heptanone; polyhydric alcohols and derivatives thereof such as monomethyl ethers, monoethyl ethers, monopropyl ethers, monobutyl ethers, or monophenyl ethers of ethylene glycol, ethylene glycol monoacetate, diethylene glycol, diethylene glycol monoacetate, propylene glycol, propylene glycol monoacetate, dipropylene glycol, or dipropylene glycol monoacetate; cyclic ethers such as dioxane; and esters such as methyl lactate, ethyl lactate, methyl acetate, ethyl acetate, butyl acetate, methyl pyruvate, ethyl pyruvate, methyl methoxy propionate, and ethyl methoxy propionate. These organic solvents may be used solely, or two or more of the organic solvents may be used in combination. Particularly, it is preferable to use the polyhydric alcohols and derivatives thereof such as the monomethyl ethers, monoethyl ethers, monopropyl ethers, monobutyl ethers, and monophenyl ethers of ethylene glycol, ethylene glycol monoacetate, diethylene glycol, diethylene glycol monoacetate, propylene glycol, propylene glycol monoacetate, dipropylene glycol, or dipropylene glycol monoacetate. These organic solvents may also be used to dilute the adhesive composition of the present invention for the purpose of, for example, adjusting its viscosity.

An amount of the organic solvent used is set as appropriate in accordance with, for example, a target viscosity and a film thickness of the adhesive composition to be applied, and is not particularly limited as long as the adhesive composition is in a concentration which is applicable to a supporting body such as a semiconductor wafer or the like. Generally, the adhesive composition is used so that a solid content concentration is in a range of 20 weight % to 70 weight %, and preferably in a range of 25 weight % to 60 weight %.

[Polymerization Reaction]

The polymerization reaction of the monomer (or copolymerization reaction, in the case of two or more monomers) may be performed by a well-known method. Therefore, the method is not limited to a specific one. The adhesive composition of the present invention is obtainable, for example, by stirring the monomer with an existing stirrer.

A temperature condition of the polymerization reaction may be set as appropriate, and is not limited. However, the temperature is preferably not less than 60 and not more than 150° C., further preferably not less than 70 and not more than 120° C.

In the polymerization reaction, a solvent may be used as appropriate. The aforementioned organic solvents can be used as the solvent. Among the aforementioned organic solvents, propylene glycol monomethyl ether acetate (hereinafter, referred to as "PGMEA") is preferable.

In the polymerization reaction, a polymerization initiator may be used as appropriate. Examples of the polymerization initiator encompass: azo compounds such as 2,2'-azobisisobutylonitrile, 2,2'-azobis(2-methylbutylonitrile), dimethyl 2,2'-azobis isobutyrate, 1,1'-azobis(cyclohexane-1-carbonitrile), and 4,4'-azobis(4-cyanovaleric acid); and organic peroxides such as decanoyl peroxide, lauroyl peroxide, benzoyl peroxide, bis(3,5,5-trimethyl hexanoyl) peroxide, succinic acid peroxide, tert-butyl peroxy-2-ethylhexanoate, t-butyl peroxypivalate, and 1,1,3,3-tetramethylbutylperoxy-2-ethylhexanoate. These polymerization initiators may be used solely, or two or more of the polymerization initiators may be used in combination as appropriate. An amount of the polymerization initiator to be used may be set as appropriate in accordance with a combination of the monomer composition, reaction conditions, and the like, and is not particularly limited.

[Film Adhesive]

The adhesive composition according to the present invention as described above may be used in various modes adoptable depending on its purpose. For example, the adhesive composition in a liquid form may be applied on a processed body such as a semiconductor wafer so as to form an adhesive layer. Alternatively, a film such as a flexible film on which an adhesive layer containing the foregoing adhesive composition of the present invention is formed in advance and dried, may be used by attaching this film (film adhesive) to the processed body (film adhesive method).

As such, the film adhesive according to the present invention includes a film, and an adhesive layer provided on the film, containing the aforementioned adhesive composition of the present invention. The content of the low-molecular-weight component being less than 0.3 weight % improves the heat resistance of the adhesive composition forming the adhesive layer, which in turn allows provision of a film adhesive excelling in its heat resistance as well as its adhesive strength in a high-temperature environment.

The film adhesive may be used such that a protection film is further provided on the adhesive layer. In this case, the adhesive layer is easily provided on a processed body by (i) stripping off the protection film which covers the adhesive layer; (ii) placing, on the processed body, the adhesive layer thus exposed, and (iii) stripping off the film from the adhesive layer.

Consequently, the use of the film adhesive allows formation of an adhesive layer having an even thickness and a good surface smoothness as compared to a case where the adhesive composition is directly applied on a processed body so as to form an adhesive layer.

The film to be used in manufacture of the film adhesive is not limited, as long as an adhesive layer formed on the film is strippable from the film and the film is a release film which can transfer the adhesive layer to a surface to be processed of a protection board, a wafer, or the like. An example of the film is a flexible film made of a synthetic resin film such as polyethylene terephthalate, polyethylene, polypropylene, polycarbonate or polyvinyl chloride, and having a thickness of 15 μm to 125 μm. It is preferable for the film to be strip-processed if necessary so that transfer can be readily carried out.

A well-known method may be appropriately used as a method for forming the adhesive layer on the film, in accordance with a desired thickness and evenness of the adhesive layer, and is not particularly limited to which method is used. For example, a well-known method may be used in which the adhesive composition according to the present invention is applied on a film so that a dried thickness of the adhesive layer is in a range of 10 μm to 1000 μm.

In a case where the protection film is to be used, the protection film to be used is not limited as long as the film is strippable from the adhesive layer. However, it is preferable for the protection film to be, for example, a polyethylene terephthalate film, a polypropylene film, or a polyethylene film. Moreover, the protective film is preferably coated with silicon or baked. This allows the protective film to be easily stripped off from the adhesive layer. A thickness of the protection film is not particularly limited, however is preferably in a range of 15 μm to 125 μm. This is because the adhesive film attached to the protective film can secure flexibility of the film adhesive.

A method of using the film adhesive is not particularly limited. For example, the following method may be taken in a case where the protection film is used: (i) the protection film is stripped off from the film adhesive, (ii) the adhesive layer thus exposed is placed on a surface of a processed body, and (iii) a heating roller is rolled on the film (back surface of the surface on which the adhesive layer is formed), so that the adhesive layer is thermally compressed onto the surface of the processed body. At this time, by sequentially rolling up the protection film on a roller such as a reel roller, the protection film that is stripped off from the film adhesive may be stored and reused.

The adhesive composition of the present invention has applications not particularly limited and may, for example, be used for various adhering purposes. However, the adhesive composition is suitably used as an adhesive composition for adhering a high-precision processing protection board of a semiconductor wafer to a substrate such as a semiconductor wafer. The adhesive composition of the present invention is particularly suitably used as an adhesive composition, when a substrate such as the semiconductor wafer is grinded so that a thickness of the substrate is reduced, for attaching the substrate to a support plate (e.g., Japanese Patent Application Publication, Tokukai, No. 2005-191550).

[Stripping Solution]

A commonly used stripping solution may be used as a stripping solution for removing the adhesive composition according to the present embodiment, however from a point of environmental burden and a stripping property, a stripping solution whose main component is PGMEA, ethyl acetate, or methyl ethyl ketone is preferably used.

[2. Method for Producing the Adhesive Composition]

The present invention provides a method of producing an adhesive composition including a polymer prepared by copolymerizing a monomer containing a polymerizable group, the method including the step of: removing, from a reaction solution containing the polymer, a low-molecular-weight component included in the polymer and having a molecular weight equivalent to 1% or less of a weight-average molecular weight of the polymer; wherein, during the step, a poor solvent is added to the reaction solution so that the polymer precipitated is recovered.

The polymer may be the polymer included in the adhesive composition of the present invention. The polymer is obtainable through the above-described polymerization reaction.

[Low-Molecular-Weight Component Removing Step]

In the low-molecular-weight component removing step, a poor solvent may be added to the reaction solution containing the polymer so that the polymer precipitated is recovered. This may be referred to as removal of the low-molecular-weight component by reprecipitation.

An example of the reaction solution is a solution prepared by dissolution of the polymer in an organic solvent. The organic solvent may be any of the organic solvents described above as used to dissolve the polymer for production of the adhesive composition of the present invention.

Examples of the poor solvent for use in the precipitation of the polymer encompass: an alcohol, an aliphatic hydrocarbon, and water. Examples of the alcohol encompass C1 to C7 alcohols such as methanol, ethanol, n-pentyl alcohol, s-pentyl alcohol, t-pentyl alcohol, isopentyl alcohol, isobutanol, isopropyl alcohol, 2-ethylbutanol, neopentyl alcohol, n-butanol, s-butanol, t-butanol, 1-propanol, n-hexanol, 2-heptanol, 3-heptanol, 2-methyl-1-butanol, 2-methyl-2-butanol, and 4-methyl-2-pentanol. Among the above, C1 to C4 alcohols are preferable, and methanol and ethanol are the most preferable.

Examples of the aliphatic hydrocarbon encompass C5 to C12 aliphatic hydrocarbons such as n-pentane, cyclopentane, 2-methylbutane, cyclohexane, n-hexane, 2-methylpentane, 2,2-dibutylbutane, 2,3-dibutylbutane, n-heptane, n-octane, isooctane, 2,2,3-trimethylpentane, n-nonane, 2,2,5-trimethylhexane, n-decane, and n-dodecane.

The above-mentioned water is not particularly limited to a specific type. For example, it is purified water or deionized water.

One of the poor solvents may be used solely, or two or more of them may be mixed for use. It is the most preferable to use a mixed solution of alcohol and water. The amount of water to be added is, with respect to alcohol, in a range of 1 mass % to 20 mass %, preferably in a range of 1 mass % to 15 mass %, and more preferably in a range of 5 mass % to 10 mass %. The above ranges allow efficient removal of the low-molecular-weight component.

Further, a polar solvent having a carbonyl group may be added to the poor solvent to an extent in which effects of the present invention are not lost. Examples of the polar solvent encompass: lactones such as γ-butyrolactone; and ketones such as methyl ethyl ketone, cyclohexanone, methyl-n-pentyl ketone, methyl isobutyl ketone, methyl isopentyl ketone, and 2-heptanone.

In the low-molecular-weight component removing step, the poor solvent may simply be added to the reaction solution, or may be added thereto while the reaction solution is stirred.

After the poor solvent is added, the polymer precipitated is recovered as appropriate. It may be filtered out, or deposited by, e.g., centrifugal separation for recovery.

The content of the low-molecular-weight component contained in the polymer after the low-molecular-weight component removing step is not particularly limited. The content is preferably less than 0.3 weight %, is more preferably not more than 0.1 weight %, is even more preferably not more than 0.01 weight %, and is most preferably 0 weight % (i.e., the low-molecular-weight component is completely removed).

The low-molecular-weight component removing step may be carried out multiple times in accordance with, for example, a target content of the low-molecular-weight component.

The polymer recovered may be washed with a poor solvent.

The polymer recovered may, for example, be dissolved again in the above-described organic solvent so that an adhesive composition is produced. Reducing the content of the low-molecular-weight component to less than 0.3 weight % allows provision of the adhesive composition of the present invention.

The following presents examples for description of the embodiments of the present invention in more detail.

The present invention clearly is not limited to the examples below and may be embodied with various details. Further, the present invention is not limited to the description of the embodiments above, but may be altered in many ways by a skilled person within the scope of the claims. An embodiment based on a proper combination of technical means disclosed in different embodiments is encompassed in the technical scope of the present invention. In addition, the contents of all the documents cited in the present specification are hereby incorporated by reference.

EXAMPLES

Note that evaluations of adhesive compositions of the following Example and Comparative Example were carried out by measuring, for each of the adhesive compositions, (i) heat resistance, (ii) adhesive strength in a high-temperature environment, (iii) an amount of gas generated (hereinafter referred to as "generated gas") at a temperature of 200° C., and (iv) crack resistance. Measuring methods of each of the items are explained below.

(Method for Measuring Heat Resistance and Generated Gas)

After applying adhesive compositions according to Examples 1 through 3 and Comparative Examples 1 and 2 later described on silicon wafers, respectively, the adhesive compositions were dried for a total of nine minute, i.e., for three minutes at a temperature of 110° C., for three more minutes at a temperature of 150° C., and for three more minutes at a temperature of 200° C. so that an applied film having a thickness of 15 µm was formed on each of the silicon wafers. Next, the thus-applied films were heated from 40° C. to 250° C. A degassing amount from each of the applied films was then measured so that evaluation was made on the heat resistance and generated gas, from the amount of gas thus measured.

Reasons why thermal resistance and moisture absorbency can be evaluated from the degassing amount are as follows. That is, the degassing amount measured until a temperature increased to 100° C., is an amount of gas derived from either water vapor or its azeotropic gas. The degassing amount measured at a temperature not less than 100° C. is derived from gas that has been generated due to decomposition of the adhesive composition caused by heat. Therefore, the thermal resistance can be evaluated from the degassing amount at a temperature of not less than 100° C., particularly around 200° C.

A TDS method (Thermal Desorption Spectroscopy method) was used for measuring the degassing amount. EMD-WA1000, manufactured by ESCO, Ltd. was used as a TDS measuring device (discharged gas measuring device).

A measuring condition of the TDS device was set as Width: 100; Center Mass Number: 50; Gain: 9; Scan Speed: 4; and Emult Volt: 1.3 KV.

The thermal resistance was evaluated at a temperature of 200° C. based on definitions as follows: "G (good)" indicates a case where a strength (Indensity) found by the TDS measuring device was not more than 100,000, and no residue was observed by a metallurgical microscope; "S (sufficient)" indicates a case where the Indensity was not less than 100,000, however no residue was observed by the metallurgical microscope; and "P (poor)" indicates a case where the Indensity was not less than 100,000 and a residue was observed by the metallurgical microscope.

The generated gas was evaluated at a temperature of 200° C. based on definitions as follows: "G" indicates a case where the strength (Indensity) found by the TDS measuring device was not more than 100,000; and "P" indicates a case where the Indensity was not less than 100,000.

(Adhesive Strength in a High-Temperature Environment)

After the adhesive compositions according to Examples 1 through 3 and Comparative Examples 1 and 2 were applied on silicon wafers, respectively, the adhesive compositions were dried for a total of nine minute, i.e., for three minutes at a temperature of 110° C., for three more minutes at a temperature of 150° C., and for three more minutes at a temperature of 200° C. Next, a glass substrate was adhered to each of the adhesive compositions at a temperature of 200° C. and with a load of 1 kg. Thereafter, each of the glass substrates was pulled so that an adhesive strength at a time when each of the glass substrates were stripped from each of the silicon wafers was found by use of a vertical model motorized stand "MX-500N" (manufactured by IMADA CO., LTD.). A case where is the adhesive strength at 250° C. is not less than 2 kg/cm$^2$ is indicated as "G (good)"; and a case where the adhesive strength is less than 2 kg/cm$^2$ is indicated as "P (poor)".

(Evaluation of Crack Resistance)

After the adhesive compositions according to Examples 1 through 3 and Comparative Examples 1 and 2 were applied on silicon wafers, respectively, the adhesive compositions were dried for a total of nine minute, i.e., for three minutes at a temperature of 110° C., for three more minutes at a temperature of 150° C., and for three more minutes at a temperature of 200° C. Next, each of the silicon wafers was subjected to a temperature of −30° C. for 30 minutes and then to a temperature of 80° C. for 30 minutes. This cycle was carried out five times. After that, the respective applied films of the adhesive compositions on the silicon wafers were evaluated by observing whether or not there were cracks therein. In a case where there were no cracks, the crack resistance was evaluated as "G (good)", whereas in a case where there were cracks, the crack resistance was evaluated as "P (poor)".

[Adhesive Compositions According to Examples 1 through 3 and Comparative Examples 1 and 2]

The adhesive compositions according to Examples 1 through 3 and Comparative Examples 1 and 2 were prepared respectively by dissolving resins A through C, A' and B' (described below) in PGMEA so that their respective contents were each 30 mass %.

The following describes a method of preparing each of resins A and B by synthesis. Table 1 shows the respective monomer compositions for polymerization of resins A and B.

TABLE 1

| Composition (parts by mass) | Resin A | Resin B |
|---|---|---|
| n-butyl acrylate | 13 | 0 |
| methyl methacrylate | 15 | 50 |
| styrene | 52 | 30 |
| dicyclopentanyl methacrylate | 10 | 0 |
| isobornyl methacrylate | 10 | 0 |
| cyclohexylmaleimide | 0 | 20 |

Example 1

The resin A was obtained as follows: Into a 300 ml four-neck flask equipped with a reflux condenser, a stirrer, a thermometer, and a nitrogen inlet tube, (i) 90 g of PGMEA as a solvent and (ii) as shown in Table 1, 15 g of methyl methacrylate, 13 g of n-butyl acrylate, 52 g of styrene, 10 g of isobornyl methacrylate, and 10 g of dicyclopentanyl methacrylate, those as monomers, were added, and blowing of N$_2$ into the flask was started. A mixture in the flask was stirred so as to initiate polymerization. While the mixture was being stirred, a temperature in the flaks was increased to 90° C. Then, a mixed solution containing 13.33 g of PGMEA and 0.6 g of t-butyl peroxy-2-ethylhexanoate (polymerization initiator) was continuously dropped via a dropping nozzle into the flask over 2 hours. The dropping speed was maintained constant.

An obtained polymerization reaction solution was left for aging at 90° C. for 1 hour. Then, a mixed solution containing 83.34 g of PGMEA and 0.3 g of t-butyl peroxy 2-ethylhexanoate was dropped into the polymerization reaction solution over 1 hour. After the polymerization reaction solution was further left for aging at 90° C. for 1 hour, 1.0 g of 1,1,3,3-tetramethylbutylperoxy-2-ethylhexanoate was added thereto at once.

The polymerization reaction was then left for aging at 90° C. for 3 hours. After a temperature of the polymerization reaction solution was increased until a reflux of the solvent was observed, the polymerization reaction solution was left for aging for 1 hour. After that, the polymerization was terminated.

[Low-Molecular-Weight Component Removing Step]

Next, the reaction solution was diluted with methyl ethyl ketone so that the solid content was about 5 mass %. Then, the reaction solution was put into a large amount of a mixed solution of methanol and water having a ratio (mass ratio) of 9:1. The resulting mixture was stirred so that resin was precipitated. The resin thus precipitated was filtered out, washed, and dried, whereby the target substance, i.e., resin A (Example 1), was obtained.

Example 2

Resin B was obtained by the same method as resin A, except that 30 g of methyl methacrylate, 52 g of styrene, and 20 g of cyclohexylmaleimide were charged as monomers and that the amount of the polymerization initiator was adjusted.

Example 3

Resin C was obtained by the same method as in Example 2, except that the mixed solution of methanol and water having a ratio (mass ratio) of 9:1 was replaced by a mixed solution of ethanol and water having a ratio (mass ratio) of 9:1.

Comparative Examples 1 and 2

Resins A' (Comparative Example 1) and B' (Comparative Example 2) were obtained by the same methods as in Examples 1 and 2, respectively, except that the low-molecular-weight component removing step was not carried out.

Table 2 shows the evaluation result of the properties such as heat resistance of each of the adhesive compositions according to Examples 1 through 3 and Comparative Examples 1 and 2. Table 2 also shows the measurement result of the respective weight-average molecular weights of the adhesive compositions.

TABLE 2

|  | Example 1 | Example 2 | Example 3 | Comparative Example 1 | Comparative Example 2 |
|---|---|---|---|---|---|
| weight-average molecular weight | 47100 | 92000 | 92800 | 45400 | 84300 |
| 1% of average molecular weight (molecular weight of low-molecular-weight component) | 471 | 920 | 928 | 454 | 843 |
| content of low-molecular-weight component (weight %) | 0.01 | 0 | 0 | 0.4 | 0.3 |
| adhesive strength in high temperature environment | G | G | G | P | G |
| generated gas | G | G | G | P | P |
| heat resistance | G | G | G | P | G |
| crack resistance | G | G | G | G | P |

The content of the low-molecular-weight components was obtained by calculating by GPC the integral value of the molecular weights each equivalent to 1% or less of the mass-average molecular weight of the polymer.

As listed in Table 2, the adhesive compositions according to Examples 1 through 3 were good in adhesive strength in a high-temperature environment, heat resistance, and crack resistance, and generation of gas from them was prevented. In contrast, the adhesive compositions according to Comparative Examples 1 and 2 were poor in adhesive strength in a high-temperature environment, and the amount of gas generated from them was large. Furthermore, the adhesive composition according to Comparative Example 1 was poor in heat resistance as well.

As described above, the adhesive composition of the present invention includes a polymer prepared by polymerizing monomer composition containing a polymerizable group, wherein: the polymer includes a low-molecular-weight component having a molecular weight equivalent to 1% or less of a weight-average molecular weight of the polymer; and the low-molecular-weight component is contained in a range of not less than 0 weight % to less than 0.3 weight % of a total weight of the polymer. This allows provision of an adhesive composition having great adhesive strength in a high-temperature environment, especially at temperatures from 140° C. to 200° C., as well as high heat resistance and favorable crack resistance.

An adhesive composition and a film adhesive according to the present invention (i) have high heat resistance, (ii) generates little gas when heated, and (iii) has high crack resistance. Hence, the adhesive composition and the film adhesive according to the present invention can be suitably used in processing of a semiconductor wafer or a chip, which processing includes a high-temperature process, a high vacuum process, and a process which uses various chemicals such as alkaline.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The invention claimed is:

1. A method of producing an adhesive composition comprising:
   preparing a polymer by polymerizing a monomer containing a polymerizable group, the monomer containing styrene in an amount of not less than 30 parts by mass but not more than 70 parts by mass where the total amount of the monomers is 100 parts by mass, and
   removing low-molecular-weight component(s) that have a molecular weight equivalent to 1% or less of a weight-average molecular weight of the polymer from a reaction solution containing the polymer, so that the total amount of all low-molecular-weight component(s) in the polymer is in a range of from 0 wt. % to less than 0.3 wt. % of the total weight of the polymer,
   wherein the step of removing comprises diluting the reaction solution with methyl ethyl ketone to obtain a diluted reaction solution, then adding to the diluted reaction solution a mixed solution of an alcohol and water comprising 1-20 wt. % of water based on the weight of the alcohol so as to precipitate the polymer, and then collecting the precipitated polymer.

\* \* \* \* \*